(12) United States Patent
Chiu et al.

(10) Patent No.: US 6,403,798 B2
(45) Date of Patent: Jun. 11, 2002

(54) METHOD FOR PREPARING OXYCODONE

(75) Inventors: Fang-Ting Chiu, Chesterfield; Young S. Lo, Chester, both of VA (US)

(73) Assignee: Boehringer Ingelheim Chemicals, Inc., Petersberg, VA (US)

(*) Notice: Subject to any disclaimer, the term of this patent is extended or adjusted under 35 U.S.C. 154(b) by 0 days.

(21) Appl. No.: 09/793,024

(22) Filed: Feb. 26, 2001

Related U.S. Application Data

(62) Division of application No. 09/607,997, filed on Sep. 22, 2000, which is a division of application No. 09/419,409, filed on Oct. 15, 1999, now Pat. No. 6,177,567.

(51) Int. Cl.$^7$ .......................................... C07D 489/00
(52) U.S. Cl. ....................................................... 546/45
(58) Field of Search ..................................... 546/44, 45

(56) References Cited

FOREIGN PATENT DOCUMENTS

| EP | 0 889 045 A1 | 1/1999 |
|----|--------------|--------|
| WO | WO 99/02529 A1 | 1/1999 |

OTHER PUBLICATIONS

Schwartz, et. al., "Efficient Synthesis of 14–Hydroxymorphinans from Codeine", Journal of Medicinal Chemistry, vol. 24, No. 12, 1981, pp. 1525–1528.*

Schwartz, Martin A. et a; Efficient Synthesis of 14–Hydroxymorphinans from Codeine; American Chemical Society; 1981; 1525–1528.

Coop, Andrew et al; Studies into the direct oxidation of codeine to 14–hydroxycodeinone; Tetrahedron; 1999; 11429–11436; vol. 55.

Singh, D.K. et al; Sythesis and characterization of in–plane and out–of–the–plane enone–lewis acid complexes; Implications for diels–Alder reactions; J. Org. Chem; 1996; 1436–1442; vol. 61.

McKillop, Alexander et al; A Simple and Efficient Procedure for the Preparation of p–Quinols by Hypervalent Oxidation of Phenols and Phenol Tripropylsilyl Ethers; J. Chem. Soc. Perkins Trans. 1; 1994; 2047–2048.

* cited by examiner

*Primary Examiner*—Alan L. Rotman
*Assistant Examiner*—Binta Robinson
(74) *Attorney, Agent, or Firm*—Robert P. Raymond; Mary-Ellen M. Devlin; Alan R. Stempel

(57) ABSTRACT

A method for the preparation of oxycodone, and salts thereof, from codeine comprising oxidation of codeine to codeinone, formation of an dienolsilyl ether congener of codeinone in strong amine base, oxidation of the dienolsilyl ether congener using peracetic acid, and hydrogenation of the resulting 14-hydroxycodeinone product.

3 Claims, No Drawings

METHOD FOR PREPARING OXYCODONE

This application is a division of prior U.S. application Ser. No. 09/607,997 filed Sep. 22, 2000, which application is a division of prior U.S. application Ser. No. 09/419,409 filed Oct. 15, 1999 now U.S. Pat. No. 6,177,567.

BACKGROUND OF THE INVENTION

1. Field of Invention

The present invention relates to an improved method for preparing oxycodone. More particularly, the present invention sets forth a method for preparing oxycodone in high yields that does not require the employment, or synthesis, of thebaine in the reaction scheme.

2. Background of the Related Art

The analgesic activity of *Papaver somniferum* has been known since antiquity. It has long been understood that the milky juice derived from the unripe seed capsules of this poppy plant possesses potent pharmacological properties. The dried and powdered form of the juice is referred to as opium. Opium comprises about 10% of the juice obtained from the unripe seed capsules of *Papaver somniferum*.

Early in the nineteenth century it was recognized that opium contains numerous alkaloid compounds. The first of these alkaloids to be isolated was morphine, described by Serturner in 1805. The isolation of other alkaloids, including codeine (Robiquet 1832), papaverine (Merck 1848), thebaine, oripavine and noscapine followed in short order. By the middle of the nineteenth century, the use of pure alkaloids rather than crude opium preparations was established medical practice. It is now known that opium contains more than twenty distinct alkaloids.

In general, the opium alkaloids can be divided into five distinct chemical classes: phenanthrene, benzylisoquinoline, tetrahydroisoquinoline, cryptopine and miscellaneous (*Remington's Pharmaceutical Sciences* 433, 1975). Therapeutically useful drugs are primarily isolated from the phenanthrene and benzylisoquinoline classes. The principal phenanthrenes are morphine (≈10% of opium), codeine (≈0.5% of opium) and thebaine (≈0.2% of opium). The principal benzylisoquinolines are papaverine (≈1.0% of opium) and noscapine (≈6.0% of opium).

Morphine itself comprises a 5-ring structure, incorporating a partially hydrogenated phenanthrene ring system. Each ring of morphine is designated as set forth below:

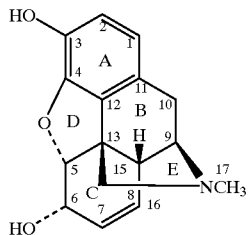

Morphine includes what is referred to in the art as a morphinan ring structure, comprising rings A, B, C and E, as set forth below:

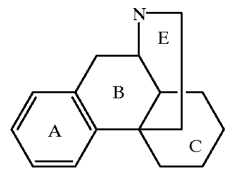

The substituent numbering of morphine derivatives follows two common conventions as shown:

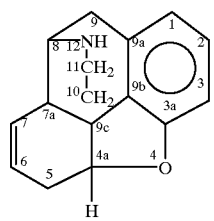

IUPAC

IUPAC

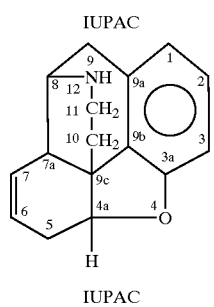

Chemical Abstracts

It is the second (Chemical Abstracts) numbering system that shall be made reference to hereinafter.

The first total synthesis of morphine was published in 1952 (Gates, et al., 74 *J. Amer. Chem. Soc.*, 1109, 1952). Because the laboratory synthesis of morphine is difficult, however, the drug is still obtained from opium or extracted from poppy straw (*Goodman & Gilman's The Pharmacological Basis of Therapeutics*, 489, 1990). Semi-synthetic derivatives of the naturally occurring opium alkaloids are widely employed in medicine today. Among the important properties of opioids that may be altered by structural modification are the affinity of the compound for various species of opioid receptors, resistance to metabolic breakdown, lipid solubility and agonist versus antagonist activity.

Codeine, hydrocodone, hydromorphone, oxycodone, and oxymorphone which are found in present day analgesic prescription drugs, are all congeners of morphine. Other structural analogs of morphine used medically in the United States include: levorphanol, nalmefene, naloxone, naltrexone, buprenorphine, butorphanol, and nalbuphine. Some morphine analogs, such as levorphanol, may be produced totally synthetically around a non-opiate morphinan nucleus which is synthesizable from coal tar derivatives (*Remington's Pharmaceutical Sciences* 1039, 1975).

Among the many morphine structural analogs used in medicine today, widespread use is made of both codeine and oxycodone.

Codeine is 3-methylated morphine. Codeine has less than one-seventh the analgesic potency of morphine (Foye, *Medicinal Chemistry*, 254 (1975)). However, as codeine has a far better oral bioavailability than morphine (the 3-methoxy group is believed to protect it from rapid first-pass biotransformation—the action of morphine orally is terminated largely by glucuronide conjugation at the 3-hydroxyl group), codeine is only less than four times as potent, on a weight basis, than morphine when both compounds are administered orally (*Drug Facts & Comparisons* 1246, 1996). While some codeine is obtained from opium directly, the quantity obtainable from such extraction is not sufficient to meet the extensive use of the alkaloid. The need for codeine is fulfilled by partial synthesis of the compound from morphine (*Remington's Pharmaceutical Sciences* 1038, 1975).

Oxycodone is a white, odorless crystalline powder of semi-synthetic origin with multiple actions qualitatively similar to those of morphine.

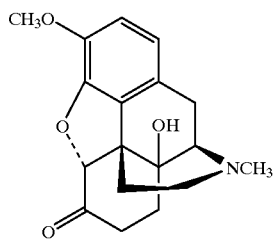

The principal actions of therapeutic value are analgesia and sedation. It is similar to codeine and methadone in that it retains at least one half of its analgesic activity when administered orally. It is a pure agonist opioid, which produces not only analgesia, but other therapeutic effects including anxiolysis, depression of the cough reflex, euphoria and feelings of relaxation. On a weight basis, oxycodone is approximately twice as potent orally as morphine (*Drug Facts & Comparisons* 1246, 1996). Oxycodone is typically indicated for the relief of moderate to moderately severe pain (*Drug Facts & Comparisons* 1259, 1996).

Thebaine, which also contains a morphinan-ring structure, differs from codeine in replacing the hydroxyl group of the morphinan C-ring with a methoxy group and the "C" ring has two double bonds—$\Delta^{6,7}$, $\Delta_{8,14}$ .(i.e., thebaine differs from morphine in that both hydroxyl groups are methylated and the "C" ring has two double bonds—$\Delta^{6,7}$, $\Delta^{8,14}$).

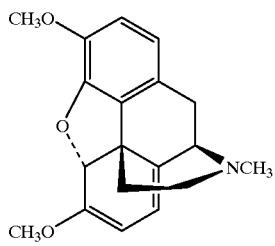

The compound demonstrates the effect that minor modifications in structure of morphinan compounds may have in pharmacological effects, as thebaine lacks any substantial analgesic activity (Foye, *Medicinal Chemistry*, 256 (1975)).

While lacking medicinal usefulness in itself, thebaine is singularly important as a key intermediate in the synthesis of many useful opiate-derivatives (See, Barber et al., 18 J. Med. Chem. 1074–107, 1975), including oxycodone (Freund et al., 94 J. Prak. Chemie 135–178, 153, 1916; See *Physician's Desk Reference*, 2569, 54th Ed. 1999), naloxone, naltrexone and nalbuphine (See, U.S. Pat. No. 4,795,813 at Col. 1, lines 16–21). Thebaine is the only known $\Delta^{6,8}$-diene compound among the naturally-ocurring morphine alkaloids (Seiki, 18 *Chem. Pharm. Bull.* 671–675, 1970).

Oxycodone may be prepared from thebaine by: dissolution of the thebaine in aqueous formic acid, oxidation treatment with 30% hydrogen peroxide (Seki, 18 *Chem. Pharm. Bull.* 671–676, 1970), neutralization with aqueous ammonia to yield 14-hydroxycodeinone and hydrogenation of the 14-hydroxycodeinone in acetic acid with the aid of a palladium-charcoal catalyst (*Remington's Pharmaceutical Sciences* 1041, 1975). Oxidation of thebaine may alternatively be performed using potassium dichromate in acetic acid (Freund et al., 94 *J. Prakt. Chem.* 135, 1916) or performic acid (Iljima et al., 60 *Helv. Chim. Acta* 2135–2137, 1977). Improved yield, however, has been reported to be obtained by oxidizing with m-chloroperbenzoic acid in an acetic acid-trifluoroacetic acid mixture (Hauser et al., 17 *J. Med. Chem.* 1117, 1974; See also, U.S. Pat. No. 4,795,813 to Schwartz, Col. 1, Lines 22–26). Yield may also be improved by hydrogenation of 14-hydroxycodeinone under a pressure of about 30 psi (Kraβnig et al. 329 *Arch. Pharm. Pharm. Med. Chem.* 325–326, 1996).

Although particularly useful in the synthesis of numerous pharmaceutical preparations, thebaine is among the least abundant phenanthrene alkaloids in *Papaver somniferum*. Due to its scarcity, a number of investigators have proposed methods of obtaining this unique alkaloid using other more abundant opioid compounds as starting materials.

Seki (18 *Chem. Pharm. Bull.* 671–676, 1970) discloses a method for preparing $\Delta^{6,8}$-diene compounds, such as thebaine, from α,β-unsaturated ketones such as codeinone, which may be obtained from the natural alkaloid codeine. Codeinone was added to a mixture of p-toluenesulfonic acid (dehydrated prior to reaction), absolute methanol and dried benzene, the solution refluxed for 3 hours under azeotropic removal of water, and the reaction mixture purified by washing with diluted sodium hydroxide, to obtain thebaine. A reported maximum yield of 26.8% was reported when using 1.1–0.15 molar equivalents of p-toluenesulfonic acid to codeinone. Eppenberger et al. (51 *Helv. Chim. Acta* 381, 1968) report a four step method for converting dihydrocodeinone to thebaine which results in a similar yield of 27%. Schwartz et al. (97 *J. Am. Chem. Soc.* 1239, 1975) demonstrate the total synthesis of thebaine in which the key step is the oxidative coupling of a reticuline derivative to a salutaridine derivative. The overall yield of dl-thebaine, however, was only in the 1–2% range based on isovanillin. Reaction of salutaridinol with an organic or inorganic acid halide or acid anhydride, followed by treatment with a strong base, is taught as a method of thebaine production in U.S. Pat. No. 3,894,026 to Sohar et al. A yield as high as 50.3% was reported (See, Col. 4, Line 29). Barber et al. (18 *J. Med. Chem.* 1074–1077, 1975) report synthesizing thebaine (as well as oripavine) from codeine and morphine. Barber et al. teach methylation of the potassium salt of codeine to give codeine methyl ether followed by oxidation with γ-MnO$_2$ (See also, U.S. Pat. No. 4,045,440 to Rapoport et al., 1977). These authors claim a 67% yield of oxycodone from codeine. European Patent Application No. EP 0 889 045 A1 likewise teaches a process for the production of thebaine from the more readily available morphinans codeine and morphine. Such method provides for converting the starting material to an alkali metal or quaternary ammonium cation and reacting the same with a compound of the formula RX wherein R is an alkyl or acyl group and X is a leaving group.

While all of the above methods have been devised to increase the supply of thebaine by synthetic and semi-synthetic means, the fact remains that thebaine remains relatively costly as opposed to morphine and codeine.

The use of thebaine as a starting material to form other therapeutically useful opioids also suffers from a disadvantage unassociated with its relative scarcity—thebaine is a known convulsant, capable of causing (even in low doses) strychnine-like convulsions (Foye, *Principles of Medicinal Chemistry* 255, 1975; The Merck Index, 9203 (11th Edition), 1989). Employment of thebaine in any synthesis scheme, therefore, entails significant risks and requires the taking of a number of precautions. Considering the relatively high cost of, and the toxicity potential of, thebaine, it would be preferred if alternative synthesis methods were developed to manufacture the many opioid congeners currently synthesized from thebaine from cheaper and less toxic materials.

U.S. Pat. No. 2,654,756 discloses a method for converting codeine into codeinone, dihydrocodeinone and dihydromorphine rather than synthesizing such compounds from thebaine. Conversion is effectuated by way of oxidation using certain ketones in the presence of aluminum alkoxides. Likewise, methods for producing 14-hydroxymorphinans, such as naloxone, naltrexone and nalbuphine (opioid antagonists) from codeine, without a thebaine intermediate, have also been disclosed (See, U.S. Pat. No. 4,472,253 to Schwarz and Schwartz and Wallace, 24 *J. Med. Chem.* 1525–1528, 1981). To date, however, no economical method has been proposed for manufacturing oxycodone from a readily available starting material that has a toxicity and cost profile which is significantly improved over that possessed by thebaine.

BRIEF SUMMARY OF THE INVENTION

The present invention provides an improved, high-yield, method for preparing oxycodone that does not require employment of a thebaine intermediate in the reaction scheme. The disclosed method makes use of compound having a morphinan-like ring structure, such as codeine or morphine, as a starting material for the synthesis of oxycodone. The method employs the steps of: converting the starting material to a compound with a morphinone ring structure, preparing a dienolsilyl ether at the C-ring of the morphinan-like ring structure by reacting an organosilyl compound with the starting material, oxidizing the silyl ether, and hydrogenating the unsaturation in the C-ring. Formation of the dienolsilyl ether is promoted by efficient dienolization of the C-ring, which is provided by reacting the α,β-unsaturated ketone and organochlorosilane reactants in the presence of a strong amine base, such as DBU (1,8-Diazabicyclo[5.4.0.]undec-7-ene) or DBN (1,5-Diazabicyclo[4.3.0]non-5-ene). Preferably the organosilyl reactant, for example a triorganosilyl chloride, is sterically hindered on the silicone atom.

An aspect of the present invention comprises a method for producing oxycodone from codeine employing two oxidation steps, one involved in the oxidation of a hydroxyl group to a ketone, and the other involving oxidative hydroxylation of a dienolsilyl ether. In particular, oxycodone free base has been produced in commercially reasonable yields by forming a dienolsilyl ether derivative of codienone in the presence of a strong amine base (preferably a diazabicyclo-base), oxidizing the silyl ether to form 14-hydroxycodeinone, and hydrogenation of the morphinan C-ring unsaturation to form oxycodone.

In one embodiment of the present invention, there is provided an improved method for synthesizing oxycodone from codeine free base. In this embodiment, codeine free base is converted to codeinone by oxidation, for example, by using a standard oxidant such as MnO$_2$, Na$_2$WO$_4$/H$_2$O$_2$, Pd(OAc)$_2$/O$_2$, and/or a standard oxidation procedure, e.g., Swern/Moffat-type oxidation (DMSO-based oxidation), Oppenauer-type oxidation (employing aluminum alkoxides and cyclohexanone or other ketones). Preferred oxidants include BaMnO$_4$ and Oppenauer oxidation. Codeinone is then reacted with an organosilyl compound having an effective leaving group, such as a halogen. The resulting dienolsilyl ether derivative is then oxidized with an oxidizing agent to afford 14-hydroxycodeinone. It has been found that the dienolsilyl ether of the morphinone C-ring may efficiently be converted to 14-hydroxycodeinone using peracetic acid solution. Hydrogenation of the unsaturation in the C-ring is subsequently performed and may be accomplished by way of, for example, pressurized catalytic hydrogenation or catalytic transfer hydrogenation in acetic acid. Oxycodone produced by such method has been found to be obtainable in yields approximating 80%.

One of the novelties of this invention is the discovery that commercially-practicable yields of therapeutically employed opioid alkaloids having a morphinan ring structure can be obtained without recourse to a thebaine intermediate by reacting a compound with a morphinone ring structure with an organosilyl reactant in the presence of a strong amine base, preferably a diazabicyclo-base such as DBU (1,8-Diazabicyclo[5.4.0.]undec-7-ene) or DBN (1,5-Diazabicyclo[4.3.0]non-5-ene) (to improve enolization and the promotion of a dienolsilyl ether derivative), followed by oxidation of the dienolsilyl ether moiety.

DETAILED DESCRIPTION OF THE INVENTION AND PREFERRED EMBODIMENTS

After considerable experimentation with numerous reaction schemes designed to form oxycodone from codeine and morphine (two relatively inexpensive opioid alkaloids), the present inventors have discovered a unique reaction scheme for manufacturing oxycodone that provides for industrially-acceptable yields. The present invention overcomes many of the prior art problems associated with the production of oxycodone and provides for a synthetic scheme for oxycodone production which does not employ the relatively costly, scarce and toxic alkaloid—thebaine.

The present inventors have discovered that enolization of the C-ring of a morphinone compound having an α,β-unsaturated ketone structure, is significantly enhanced by exposure to a strong amine base, such as DBU or DBN and similar diazabicyclo-bases. Formation of the dienolsilyl ether (by reaction with the ketone of such ring with a organosilyl compound having an effective leaving group) was greatly improved by effectuating the reaction in the presence of the strong amine base. The present inventors have further discovered that the dienolsilyl ether of codeinone (the silyl ether formed at position 6 (chemical abstract substituent-numbering designation)) may be used to directly form 14-hydroxycodeinone by oxidation of the silyl ether. In a preferred embodiment, oxidation is performed at room temperature for about 3 hours. The dienolsilyl ether of codeinone may be dissolved in toluene or other similar solvent. Oxidation may be efficiently performed with relatively high yield using peracetic acid or other peracids. Hydrogenation of 14-hydroxycodeinone produces oxycodone. A preferred hydrogenation reaction employs hydrogen gas or $NaH_2PO_2$ along with a palladium-carbon catalyst, with the 14-hydroxycodeinone being dissolved in a weakly acidic solution such as aqueous acetic acid.

A codeinone dienol silyl ether, such as the intermediate compound formed in the conversion of codeine to oxycodone according to certain embodiments of the present invention, is disclosed in pending European patent application No. EP 0 889 045 A1 to Jen-Sen Dung. The reference, however, is instructive as to the unobviousness of the present invention.

Recognizing the expense and relative scarcity of thebaine, EP 0 889 045 A1 teaches (as noted above) a process for the production of thebaine and analogues thereof. While disclosing codeinone tert-butyldimethylsilyl dienol ether (Example 6), the patent teaches the production of oxycodone only from thebaine which is synthesized by the procedures described (See, e.g., Abstract of the Disclosure, Col. 1, Lines 25–52, Col. 5, Lines 24–29, Col. 9, Example 8). No recognition is made of the fact that the tert-butyldimethylsilyl dienol ether could be utilized, without synthesis of a thebaine intermediate, to produce oxycodone. Further the reference fails to teach a method for producing organosilyl dienol ethers of the morphinone ring in commercially practicable yields. The reference notes that the codeine tert-butyldimethylsilyl dienol ether produced by the methods described comprised only 23% of the solid mass recovered (thus comprising a relatively minor component of the solid mass). EP 0 889 045 A1 does not disclose or imply that yield could be significantly enhanced by the presence of strong amine base (rather than tetrahydrofuran as taught by the reference) in the reaction mix when the ether is being formed.

The presently disclosed invention provides commercially practicable yields, yields typically in excess of 50%, and more typically in excess of 80%, of oxycodone from codeinone (a compound that is easily obtained from codeine by oxidation). Codienone is easily synthesized from codeine, an alkaloid that can be obtained naturally, or semi-synthetically, as from morphine. It has been discovered that by reacting an organosilyl compound in the presence of a strong amine base that a high degree of conversion to the organosilyl dienol ether conjugate of codeinone may be achieved. The strong amine base is believed to strong favor enolization of codeinone, a compound having an α,β-unsaturation in the "C" ring of the morphinone ring structure, while the organosilyl moiety captures the enol form. The organosilyl ether form of codeinone is also promoted by employing an organosilyl compound having an effective leaving group, such as a halogen, and in employing a stericly bulky silicone moiety. While the resulting dienol-silyl ether form of codeinone may be oxidized to 14-hydroxycodeinone using a number of standard oxidizing agents, it has been found that oxidation with peracetic acid is extremely efficient, producing about an 80% yield. The 14-hydroxycodeinone is then hydrogenated, as by catalytic hydrogenation, so as to hydrogenate the α,β-unsaturation of the C-ring. A catalytic transfer hydrogenation method in aqueous acetic acid was found to produce about the same yield, and similar impurity patterns, as the method reported by R. Kraβnig, et al.

In an aspect of the invention, there is disclosed a method of producing oxycodone from codeinone which comprises the steps of: (a) producing a dienol organosilyl ether at position 6 of the C-ring of codeinone thereby forming a dienol organosilyl ether congener of codeinone; (b) oxidizing the dienol organosilyl ether to form 14-hydroxycodeinone; (c) hydrogenating the unsaturation in the C-ring of 14-hydroxycodeinone to produce oxycodone.

The dienol organosilyl ether congener of codeinone is preferably formed by reacting an organosilyl compound with codeinone, such organosilyl compound having the formula:

$$R_3{}^3SiX$$

wherein $R^3$ is alkyl or aryl and the three $R^3$ groups may be the same or different and X is a leaving group, such as imidazole, mesylate, tosylate or a halogen. Preferably, the organosilyl compound is reacted with codeinone in the presence of a strong amine base, such as diazobicyclo-base, for example, DBU (1,8-Diazabicyclo[5.4.0.]undec-7-ene) or DBN (1,5-Diazabicyclo[4.3.0]non-5-ene). Oxidation of the dienol organosilyl ether may be performed by treating the dienol organosilyl ether congener of codeinone with peracetic acid, preferably in the presence of an organic solvent such as toluene.

In another aspect of the present invention there is disclosed a method for oxidizing a dienol silyl ether selected from the group having the formula:

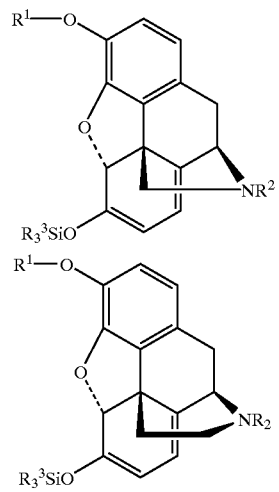

wherein $R^1$ is selected from the group of alkyl or acyl and $R^2$ is selected from the group of lower alkyl, allyl, or lower alkyl substituted by cycloalkyl, and $R^3$ is an alkyl or aryl group and the three $R^3$ groups may be the same or different, which comprises the steps of: (a) reacting the dienol silyl ether compound with peracetic acid and (b) thereafter a work up procedure to isolate the product as a free base.

In yet another aspect of the present invention there is disclosed a method for forming a dienol silyl ether selected from the group having the formula:

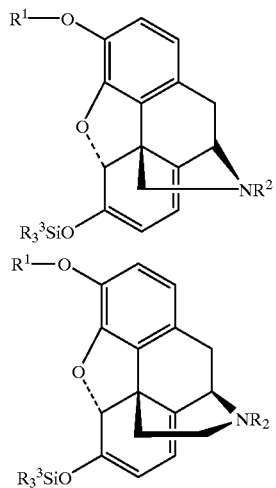

wherein $R^1$ is selected from the group of alkyl or acyl and $R^2$ is selected from the group of lower alkyl, allyl, or lower alkyl substituted by cycloalkyl, and $R^3$ is an alkyl or aryl group and the three $R^3$ groups may be the same or different, which comprises the steps of:

reacting an morphinan-6-one selected from the group having the formula:

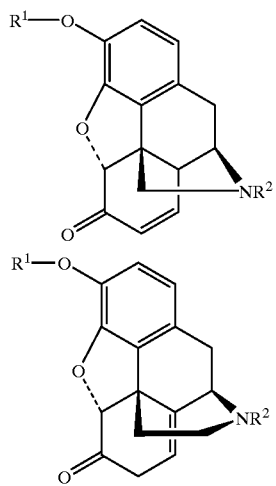

with an organosilyl compound having the formula

$R_3^3SiX$ wherein $R^3$ is an alkyl or aryl group and the three $R^3$ groups may be the same or different group and X is a leaving group, such as imidazole, mesyate, tosylate or a halogen, in the presence of a strong amine base. The strong amine base may be a diazabicyclo-base, and may be more specifically be selected from the group consisting of: DBU (1,8-Diazabicyclo[5.4.0.]undec-7-ene) and DBN (1,5-Diazabicyclo[4.3.0]non-5-ene). X is preferably chloride.

And yet another aspect of the present invention entails a method of producing oxycodone from codeine which comprises the steps of: (a) oxidizing codeine to codeinone; (b) producing a dienol organosilyl ether at position 6 of the C-ring of codienone thereby forming a dienol organosilyl ether congener of codeinone; (c) oxidizing the dienol organosilyl ether to form 14-hydroxycodeinone; (d) hydrogenating the unsaturation in the C-ring of 14-hydroxycodeinone to produce oxycodone. The dienol organosilyl ether congener of codeinone of this embodiment may be formed by reacting an organosilyl halide with codeinone, preferably an organosilyl halide having the formula: $R^3_3SiCl$, wherein $R^3$ is as defined hereinabove. Preferably the organosilyl chloride is reacted with codeinone in the presence of a strong amine base. The strong amine base may be a diazabicyclo-base and may be selected from the group consisting of: DBU (1,8-Diazabicyclo[5.4.0.]undec-7-ene) or DBN (1,5-Diazabicyclo[4.3.0]non-5-ene). The oxidation of the dienol organosilyl ether may be performed by treating the dienol organosilyl ether congener of codeinone with peracetic acid (which reaction may be carried out in the presence of an organic solvent such as toluene).

A preferred method of the present invention for forming oxycodone from codeine fundamentally involves four (4) synthetic steps: (1) oxidation of codeine to codeinone; (2) formation of an organosilyl ether congener of codeinone; (3) oxidation of the silyl ether to 14-hydroxycodeinone; and (4) hydrogenation of the partially unsaturated non-aromatic C-ring to produce oxycodone, such as described in more detail below and as shown in the following diagrammatic form:

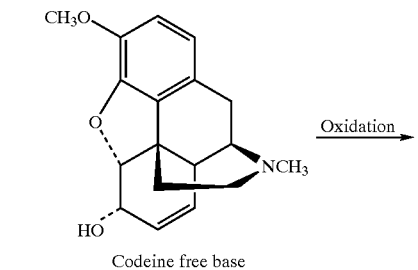

Codeine free base

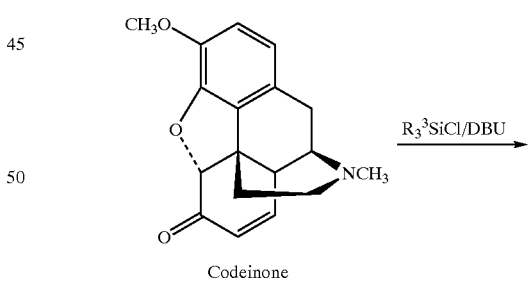

Codeinone

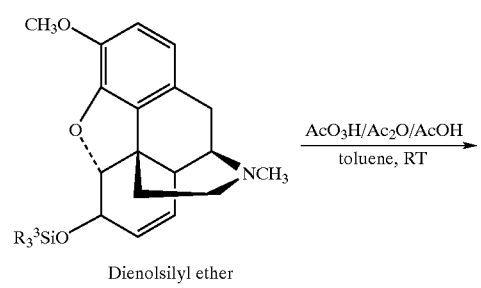

Dienolsilyl ether

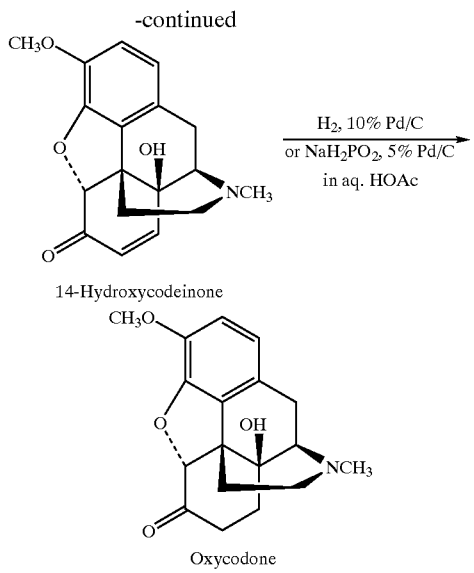

Oxidation of Codeine to Codeinone

The oxidation of codeine to codeinone may be performed by numerous methods known to those of ordinary skill in the art including: $CrO_3$/TBHP oxidation, dichromate oxidation, $Na_2WO_4$/peroxide oxidation, $BaFeO_4$ oxidation, hydrous $ZrO_2$/ketone oxidation, oxidation using $CrO_2$, Highet oxidation (Highet et al., 77 *J. Am. Chem. Soc.* 4399, 1955) using manganese dioxide, Oppenauer oxidation using aluminum isopropoxide and cyclohexanone (See, U.S. Pat. No. 2,654,756 to Homeyer et al.), sodium tungstate activated peroxide oxidation (Sato et al., 119 *J. Am. Chem. Soc.* 12386, 1997), Swern/Moffatt type (DMSO-based) oxidation, palladium acetate catalyzed aerobic oxidation and barium manganate oxidation (See, Nishimura et al., 39 Tet. Let. 6011).

As would be understood by one of ordinary skill in the art, with respect to any oxidation procedure, adjustment of reaction conditions, such as the concentration of the reactants, the acidity of the reaction mixture, the presence or absence of solvating agents, and the like, .may impact upon the yield of oxidized product. For example, with respect to barium manganate oxidation it may be preferred to keep the reaction mixture at about 0° C. and to control the polarity of the solvent to improve yield. With respect to Oppenauer oxidation, the addition of toluene to the reaction scheme may improve yield, as well may azeotropic removal of water from the codeine/toluene solution prior to the addition of a catalytic amount of aluminum isopropoxide, and the collection of distillate during and after the addition of the aluminum isopropoxide. Selection may also be made between numerous potential reactants such as in Swern/Moffatt type oxidation numerous activators in DMSO may be employed including: oxalyl chloride, TsCl, $P_2O_5$, TFAA, $Ac_2O$, $PySO_3$, $Ts_2O$, $SOCl_2$, DCC, DIPC, cyanuric chloride, $ClSO_2NCO$, $(MeSO_2)_2O$, $Cl_2$, hot air, and the like.

Formation of Dienolsilyl Ether of Codeinone

Codeinone may be modified to form a silyl ether at position 6 (Chemical Abstracts designation) by reaction with an organosilyl compound $R_3{}^3SiX$. Preferred organosilyl compounds were found to be stericly-hindered at the silicon atom and to have chlorine as the leaving group. The enolized codeinone was efficiently trapped with a trialkychlorosilane, such as tert-butyldimethylchlorosilane or triethylchlorosilane. The trimethylsilyl ether, however, was found to be rapidly hydrolyzed. Enolization of codeinone, and the formation of the dienolsilyl ether, was found to be promoted by the presence of strong amine base, such as DBU or DBN. Other bases such as LDA, DABCO, DIPEA, TEA, imidazole, N-methylmorpholine, HMDS-Li salt, hexamethyldisilazane, and aluminum isopropoxide did not yield a desirable amount of dienolsilyl ether.

Oxidation of Dienolsilyl Ether of Codeinone to 14-Hydroxycodeinone

Oxidation of the dienolsilyl ether of codeinone to 14-hydroxycodeinone may be performed using the many oxidizing agents and methods known in the art. For example, the dienolsilyl ether may be oxidized in a hydrogen peroxide-free performic acid mixture according to the method published by Swern (D. Swern, *Organic Reactions VII*, 378, 1953), by way of $MnO_2$ or performic acid. A preferred oxidation procedure, however, was found to employ peracetic acid prepared from acetic anhydride, hydrogen peroxide and a catalytic amount of sulfuric acid. Aging of the peracetic acid solution and treatment with acetic anhydride was found to improve optimum oxidation hydroxylation) presumably by removal of any free hydrogen peroxide. Anhydrous peracetic acid up to 25 days old was found to be most effective. The yield of 14-hydroxycodeinone was found to be also effected by the molar ratio and percentage of oxidant in the mixture. Optimal oxidation conditions may vary with different organosilyl ethers. For example, the presence of trifluoroacetic acid (TFA) was found to improve the oxidation of the triethyl-silyldienolate of codeinone. The isolation of 14-hydroxycodeinone may entail de-activation of the spent peracetic acid by treating with either sodium hydrogen sulfite or sodium thiosulfate aqueous solution, and removal of acetic acid solvent (in vacuo), and organic neutral by-products like disiloxane or silanol and N-oxide, by acid/base work up procedures. Oxidation of either t-butyldimethylsilyldienolate or triethylsilyldienolate of codeinone may afford a similar yield of 14-hydroxycodeinone (or its acid salt). Oxidation of the triethylsilyl dienol ether and t-butyldimethylsilyl ether of codeine with peracetic acid was found to produce yields of 14-hydroxycodeinone in excess of about 80%.

Hydrogenation of 14-Hydroxycodeinone to Oxycodone

14-Hydroxycodeinone was converted to oxycodone by hydrogenation of the α,β-unsaturation in the C-ring. Hydrogenation may be performed by using any of the methods known for hydrogenation of 14-hydroxycodeinone to oxycodone. For example, diphenylsilane and $Pd(Ph_3P)/ZnCl_2$ may be used to reduce 14-hydroxycodeinone, as may sodium hypophosphite in conjunction with a Pd/C catalyst in aqueous acetic acid, and Pd/C catalytic transfer hydrogenation.

The following examples illustrate various aspects of the present invention. They are not, however, to be construed as limiting the claims in any manner whatsoever.

EXAMPLE 1

Formation of Codeinone from Codeine

Codeinone was prepared by oxidation of codeine sulfate trihydrate. A reaction mixture was prepared containing codeine sulfate trihydrate (10.4 g), de-ionized water (20 g) and isopropyl acetate (87.2 g) at ambient temperature. The reaction mixture was agitated and the resultant mixture cooled to about 20±5° C. Concentrated ammonium hydroxide (18.0 g) was added in several portions and the mixture was maintained at a temperature of about 20±5° C. with stirring. Stirring was continued for about 15 minutes, and then a small portion of the aqueous layer was withdrawn to check for pH value, which was to be advantageously maintained between 11.0 and 12.0. The aqueous layer was then separated and re-extracted with isopropyl acetate (35 g). The combined organic layers (isopropyl acetate) were concentrated in vacuo to near dryness at temperature NMT 45° C. The residual isopropyl acetate solvent was chased by adding 18 g of toluene. The concentration process was then repeated in vacuo. Codeine free base dissolved in a mixture of toluene (177 g) and cyclohexanone (47.4 g) at temperature NMT 45° C. was then transferred to the reaction flask which was equipped with magnetic stirrer, thermocouple, Dean-Stark trap with condenser attached, addition funnel with an extender (about 4 inches height), and a nitrogen-inlet adapter. The mixture was heated to boiling temperature (about 116–118° C.) under a nitrogen atmosphere and 26 g (30 ml) of distillate were collected in the Dean-Stark trap. A solution of aluminum isopropoxide (3.5 g) in 35.5 g (41 ml) of toluene was then added to the addition funnel. The heating rate was adjusted and the aluminum isopropoxide/toluene solution was added into the reaction mixture at such a rate that the total volume was added over a 10–20 minute period (approximately the same volume (41 ml) of distillate was collected in the Dean-Stark trap). After completion of the addition, collection of the distillate was continued such that 57 g (66 ml) of distillate was collected in the Dean-Stark trap at a similar distillation rate. The heat source was removed and the mixture allowed to cool down to ambient temperature (under nitrogen atmosphere) over a period of about 30 minutes. Reaction completeness was determined by withdrawing a small sample from the batch, extracting it with a saturated sodium bicarbonate solution and ethyl acetate, concentrating the organic layer, re-dissolving it with the HPLC mobile phase, and analyzing the sample on HPLC. The reaction was considered complete if the area % of codeine was less than 3.5A %.

An aqueous solution of 13 wt. % Rochelle salt was then prepared by dissolving 19.5 g of potassium sodium tartrate tetrahydrate in 130.5 g of de-ionized water at 20±5° C. The aqueous Rochelle salt solution (90 ml) was added into the reaction mixture in one portion at ambient temperature, the batch stirred for about 10 minutes, and filtered. Both layers were saved. The organic layer was washed with 60 ml of aqueous Rochelle salt solution (both layers were saved). The organic layer was washed with a mixture of 30 ml brine solution and 30 ml 5% sodium bicarbonate solution (both layers were saved). All aqueous layers were then combined and extracted with 43 g (50 ml) of toluene. The aqueous layer was discarded. The organic layers were then combined and concentrated in vacuo at temperature NMT 55° C. to near dryness. Twenty-two grams (25 ml) of toluene was added and the resultant organic layer concentrated in vacuo twice more to remove residual cyclohexanone. Subsequently, 11.8 g (15 ml) of 2-propanol was added and the mix slurried at 0–5° C. for at least eight hours under a nitrogen atmosphere. Solids were then filtered and the flask/wet cake rinsed with the chilled (about 5° C.) recycled filtrate. The latter operation was repeated until no solids were left in the flask. The chilled wet cake was then rinsed with chilled (5–10° C.) 2-propanol (12 g, 15 ml), and filter dried. The wet cake was then rinsed with heptane (6.8 g, 10 ml) and filter-dried. The resulting solids were vacuum dried at temperature NMT 50° C. to a constant weight. A yield of 5.2 to 6.45 g (65.4 to 81.2%) of off-white solids, with HPLC purity of about 96A %–99.3A % was obtained. The compound was stored in a dark and cool place.

EXAMPLE 2

Preparation of Dienolsilyl Ether of Codeinone

Codeinone (6.0 g) with toluene (104 g) was added to a reaction flask equipped with a mechanical stirrer, thermocouple, Dean-Stark trap with condenser attached, and a nitrogen-inlet adapter. The batch was heated to reflux and about 27.7 g (32 ml) of distillate was collected in the Dean-Stark trap. The contents were then cooled to 20±5° C. under a nitrogen atmosphere. A solution of DBU (4.22 g) in toluene (3 g) was added in one portion. Subsequently, a solution of t-BDMSiCl (4.22 g) in toluene (5 g) was likewise added in one portion. The batch was slowly warmed to 58±3° C. and stirred at this temperature for about 2 hours. Completion of the reaction was adjudged by withdrawing a small sample from the batch, extracting it with a mixture of ethyl acetate and saturated sodium bicarbonate solution, spotting the organic layer on a TLC plate, and then eluting it with a mobile phase of 9:1 mixture of dichloromethane and methanol plus 3–4 drops of concentrated ammonium hydroxide. If the reaction was determined to be incomplete, stirring was continued at 58±3° C. for an additional 2 hours and a TLC check performed once more. Alternatively reaction completion was accomplished by adding about 5–10% more of both DBU and tBDMSiCl to the reaction mixture at the same temperature. The contents were then cooled to 20±5° C., and a mixture of 5% sodium bicarbonate solution (80 ml) and 60 ml of water was added in one portion. Stirring continued for about 10 minutes. The aqueous layer was then separated and discarded. The organic layer was washed with a mixture of 50 ml brine and 50 ml saturated ammonium chloride solution (the aqueous layers were discarded). The organic layer was concentrated to near dryness in vacuo at temperature NMT 50° C., and the residue diluted with 33.2 g of toluene to make up a 20 wt. % stock solution. Yield was approximately quantitative. The stock solution was found to be stable at ambient temperature under nitrogen atmosphere for at least 6 months.

EXAMPLE 3

Preparation of Peracetic Acid Solution

14-Hydroxycodeinone was synthesized from the dienolsilyl ether of codeinone by oxidative hydroxylation using a peracetic acid solution preparation. The peracetic acid solution was prepared as follows:

$$(CH_3CO)_2O \ + \ 30\% \ H_2O_2 \ + \ HOAc \xrightarrow[\text{RT}]{\text{cat. } H_2SO_4}$$

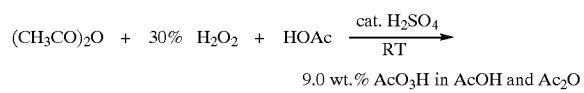
9.0 wt.% AcO$_3$H in AcOH and Ac$_2$O

Acetic anhydride (80.0 g) and concentrated sulfuric acid (0.15 g, or about 6 drops) at ambient temperature were added to a clean and dried round bottom flask (3-neck, 250 ml) equipped with mechanical stirrer, thermocouple, nitrogen-inlet adapter and addition funnel. The mixture was cooled to about 10±3° C. under a nitrogen atmosphere. A 14.0 g of 30% aqeous hydrogen peroxide solution was slowly added through the addition funnel. The addition of hydrogen peroxide was performed drop by drop maintaining content temperature at NMT 27° C. (formation of peracetic acid and the hydrolysis of acetic anhydride are strongly exothermic, cooling is absolutely essential, but over-chilling the batch is not recommended). After complete addition, the batch was stirred for about 30 minutes in a 10±3° C. bath. Acetic acid (10.0 g) was then added through the addition funnel, and the batch slowly warmed to 25±5° C. The batch was then stirred for an additional hour (the batch should be kept in water bath all the time in order to avoid any unexpected exotherm).

EXAMPLE 4

Preparation of 14-Hydroxycodeinone from Dienolsilyl Ether of Codeinone

Peracetic acid solution (107.7 g of 9.0 wt. % peracetic acid) at ambient temperature (22±5° C.) was added to a reaction flask (3-neck, 500 ml) equipped with mechanical stirrer and thermocouple, nitrogen-inlet adapter and addition funnel. A 20 wt. % stock solution of the dienolsilyl ether of codeinone (41.7 g) was added through the addition funnel over a period of about 5 minutes and the temperature of the contents maintained at NMT 28° C. The batch was stirred at 22±5° C. for at least 3 hours. In order to test reaction completeness, a small sample was withdrawn from the batch and quenched with saturated sodium bicarbonate solution, and extracted with ethyl acetate. The EtOAc layer was spotted onto a TLC plate and subsequently checked for the disappearance of starting dienolsilyl ether of codeinone. The TLC mobile phase was a mixture of 95:5 of dichloromethane and methanol plus 3-5 drops of concentrated ammonium hydroxide. If the reaction was adjudged incomplete, the mixture was stirred at the same temperature for an additional 2 hours then analyzed by TLC again. Alternatively completion of the reaction was pushed by the addition of 10 g of peracetic acid (9.0 wt. %) and stirring for an additional 1 h (analysis was then once more preformed using TLC).

Upon determination of the completion of the reaction 20.0 g of 10 wt. % of aqueous sodium hydrogen sulfite solution was added in one portion, and the resultant admixture stirred for 10 minutes at ambient temperature. The batch was then concentrated in vacuo at temperature NMT 45° C. to dryness. Subsequently water (180 g), toluene (69 g), ethyl acetate (36 g) were added and vigorous stirring for about 10 minutes undertaken. The resulting layers were separated and the aqueous layer saved in a flask. The organic layer was washed thrice with a solution of 26 ml of 2.5% HCl. The combined aqueous layers were then filtered through a pad of wet (with water) hyflo-supercel filter aid. Subsequently, EtOAc (85 g) was added to the filtrate and concentrated ammonium hydroxide added in a quantity to adjust the pH of the aqueous layer to about 11. The mixture was stirred for 10 minutes at about 60° C. and the layers were separated and saved. The aqueous layer was washed with EtOAc (50 g) and then discarded. The combined organic layers were concentrated in vacuo to dryness at temperature NMT 50° C. To the residue was added 2-propanol (13 g), and the resultant mixture stirred at 5–10° C. for at least 5 hours. The solids were filtered, the flask and solids rinsed with the chilled (5° C.) filtrate followed by chilled (5–10° C.) 2-propanol (10 g) and heptane (8 g). The solid was then vacuum dried at temperature NMT 50° C. to a constant weight. A yield of between 3.50–4.96 g (55%–78%) of 14-hydroxycodeinone free base with a purity of over 96A % was obtained.

EXAMPLE 5

Preparation of Oxycodone from 14-Hydroxycodeinone by Catalytic Hydrogenation

14-Hydroxycodeinone (4.98 g) and acetic acid (155 g) were added to a Parr shaker equipped with hydrogen inlet and outlet connectors. The mixture was shaken for about 5 minutes to completely dissolve the 14-hydroxycodeinone at ambient temperature. The system was then evacuated and the Parr shaker was filled with nitrogen. In one portion, under the nitrogen atmosphere, 10% Pd/C (50% water wet, 4.0 g) was added. The system was then evacuated, and was filled with hydrogen gas to a pressure of about 38 psi. The hydrogen inlet from the supply tank was then closed and the mixture was shaken at an initial pressure of 38 psi for about 3 hours (at ambient temperature). After 3 hours of shaking, the system was evacuated and filled with nitrogen. The contents were filtered over a hyflo-supercel filtering pad (3 g, wetted with water). The Parr bottle and wet cake were then rinsed with acetic acid (2×21 g). The filtrate was concentrated in vacuo to dryness at temperature NMT 50° C. The residue was then dissolved with de-ionized water (50 g), and the pH adjusted to about 11.0 to 12.0 using 20% aqueous KOH solution and concentrated ammonium hydroxide (4 g). The mixture was then extracted with ethyl acetate (4×135 g), and the combined organic layers concentrated in vacuo to dryness. A yield of 3.51 to 4.26 g of crude oxycodone with HPLC purity of over 85A % (70.0 to 85.0% yield) was obtained.

EXAMPLE 6

Preparation of Oxycodone from 14-Hydroxycodeinone by Catalytic Transfer Hydrogenation Method 14-Hydroxycodeinone (4.98 g) and acetic acid (137 g) were added to a reaction flask (3-neck, 250 ml) equipped with mechanical stirrer, addition funnel, thermocouple and nitrogen-inlet adapter. The system was evacuated and the flask filled with nitrogen. Subsequently, 5% Pd/C (50% water wet, 3.0 g) in one portion was added under the nitrogen atmosphere. While the mixture was stirred for about 5 minutes at ambient temperature (22±5° C.), a solution of sodium hypophosphite (6.0 g) in de-ionized water (25 g) was prepared. The aqueous sodium hypophosphite solution was transferred into the addition funnel, and added to the reaction mixture over a period of about 30 minutes with maintenance of content temperature at about 22±5° C. The mixture was then warmed to about 45° C. and stirred for about 1 hour.

To determine the completeness of the reaction, a small sample was withdrawn from the batch and the sample was filtered by means of a syringe filter into a mixture of ethyl acetate and saturated sodium bicarbonate solution. After extraction, the organic layer was concentrated to dryness and the residue dissolved with HPLC mobile phase. The disappearance of 14-hydroxycodeinone was determined. If the reaction was discerned to be incomplete, the batch was stirred for an additional 2 h period at 45° C., and the HPLC check performed once more.

Upon determination that the reaction was complete, the batch was cooled to ambient temperature (22±5° C.) under the nitrogen atmosphere, and the contents filtered over a hyflo-supercel filtering pad (3.0 g, wetted with water). The flask and wet cake were rinsed with acetic acid (20 g). The filtrate was concentrated in vacuo to near dryness at temperature NMT 50° C. The residue was dissolved with de-ionized water (50 g) and the pH adjusted to 11.0 to 12.0 with 20% aqueous KOH solution and concentrated ammonium hydroxide (about 4 g). The mixture was then extracted with ethyl acetate (4×135 g) and the combined organic layers concentrated to dryness in vacuo. Crude oxycodone with an HPLC purity of over 85A % was obtained in a yield of 70.0 to 85.0% (3.51 to 4.26 g).

While the invention has been described with respect to preferred embodiments, those skilled in the art will readily appreciate that various changes and/or modifications can be made to the invention without departing from the spirit or scope of the invention as defined by the appended claims.

What is claimed is:

1. A process of producing 14 hydroxycodeinone from codeinone comprising reacting organosilyl halide in the presence of diazobicyclo-base and oxidizing the resulting product with peracetic acid.

2. The process of claim 1 wherein the diazobicyclo-base is selected from the group consisting of:
   DBU (1,8-Diazabicyclo [5.4.0] undec-7-ene) and DBN (1,5-Diazabicyclo [4.3.0] non-5-ene).

3. A method for oxidizing a dienol silyl ether selected from the group having the formula:

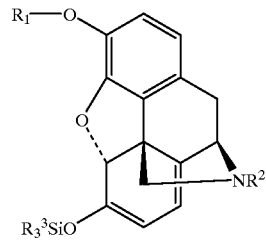

wherein $R^1$ is alkyl or acyl, $R^2$ is lower alkyl, allyl or lower alkyl substituted by cycloalkyl, and $R^3$ is an alkyl or phenyl group and the three $R^3$ groups are the same or different which comprises the steps of:

a) reacting the dienol silyl ether compound with peracetic acid and b) thereafter isolating the product as a free base.

* * * * *